United States Patent [19]

Hibino

[11] Patent Number: 5,243,967
[45] Date of Patent: Sep. 14, 1993

[54] ENDOSCOPE SYSTEM PROVIDING MUTUAL OPERATIVE COMMUNICATION BETWEEN THE DRIVE CONTROL MEANS AND THE VIDEO SIGNAL CONTROL MEANS

[75] Inventor: Hiroki Hibino, Hachioji, Japan

[73] Assignee: Olympus Optical Co., Ltd., Tokyo, Japan

[21] Appl. No.: 834,656

[22] Filed: Feb. 12, 1992

[30] Foreign Application Priority Data

Mar. 26, 1991 [JP] Japan .................................. 3-62113

[51] Int. Cl.$^5$ .......................... A61B 1/06; A61B 1/00; H04N 7/18
[52] U.S. Cl. .......................................... 128/6; 128/4; 358/98
[58] Field of Search ................ 358/98; 354/62; 128/4, 128/6–8, 11; 175/45

[56] References Cited

U.S. PATENT DOCUMENTS

| | | |
|---|---|---|
| 4,499,895 | 2/1985 | Takayama . |
| 4,559,928 | 12/1985 | Takayama . |
| 4,621,618 | 11/1986 | Omagari . |
| 4,899,731 | 2/1990 | Takayama et al. ............ 128/4 |
| 4,941,456 | 7/1990 | Wood et al. . |
| 5,018,509 | 5/1991 | Suzuki et al. ............ 128/6 |

FOREIGN PATENT DOCUMENTS 57-148928 9/1982 Japan .
59-181122 10/1984 Japan .

Primary Examiner—Richard J. Apley
Assistant Examiner—John P. Leubecker
Attorney, Agent, or Firm—Armstrong, Westerman, Hattori, McLeland & Naughton

[57] ABSTRACT

The principal object of the present invention is to provide an endoscope system for making endoscope system operating information easily available and ensuring improved operability. The endoscope system comprises an endoscope to be inserted into body cavities, a light source for supplying illumination light, an air and water, and suction unit for supplying air and water, and sucking up contaminants from body cavities, a motor control unit for driving and controlling a motor for bending, a camera control unit for processing video signals originating from a solid-state imaging device in the endoscope, a monitor for displaying video signals, a VTR for recording the video signals, and a remote control for remotely operating the motor control unit. A motor control unit control circuit in the motor control unit and a camera control unit control circuit in the camera control unit communicate with each other for mutual control.

34 Claims, 13 Drawing Sheets

ENDOSCOPE SYSTEM PROVIDING MUTUAL OPERATIVE COMMUNICATION BETWEEN THE DRIVE CONTROL MEANS AND THE VIDEO SIGNAL CONTROL MEANS

BACKGROUND OF THE INVENTION

1. Field of the Invention

The present invention relates to an endoscope system having a means for driving and controlling an endoscope drive for bending and a means for controlling a means for converting image signals originating from an endoscope into video signals.

2. Description of the Related Art

In recent years, endoscopes have been widely adopted for medical and industrial purposes.

These endoscopes are divided into two types: one type of endoscopes has a rigid insertion tube which is inserted into the abdominal cavity under guidance of a cannula similar to a tracheal cannula for puncturing the abdomen, and the other type has a flexible insertion tube which does not require a puncturing procedure but is routed from the oral cavity or anus through a curved body cavity to an intended region.

When the flexible endoscope is inserted from the anus to the large intestine, it must be routed through an S-shaped curved path to a deep region in a body cavity. This requires tremendous experience and skill. Therefore, unless an operator is an expert, he/she will cause a patient a great pain.

To solve the aforesaid problem, a variety of endoscopes of prior art have been proposed. In the prior art, a means for propelling an insertion tube is installed at the distal end of the insertion tube of an endoscope so that the insertion tube can be inserted to deep regions.

For example, as disclosed in Japanese Patent Laid-Open No. 1984-181122, an insertion drive and a rotation drive are incorporated in an insertion tube. The inserting and rotating speeds at which an expert inserts an insertion tube are time-sequentially stored in memory. The stored data of the inserting and rotating speeds is used to control the insertion and rotation drives, so that the insertion tube can be inserted automatically.

As proposed in Japanese Patent Laid-Open No. 1990-178525, a bending rate as well as inserting and rotating speeds is stored in memory, then used to control the insertion, rotation, and bending drives. Thus, the insertion tube is automated.

Although the above endoscope systems of prior art have the full-fledged functions as a whole, they are difficult to operate. Thus, the system operability has posed a problem.

SUMMARY OF THE INVENTION

The principal object of the present invention is to provide an endoscope system for making endoscope system operating information easily available and ensuring safety and excellent operability, wherein a means for driving and controlling an endoscope drive and a means for controlling conversion from endoscope images into video signals communicate mutually.

An endoscope system of the present invention comprises an endoscope having an insertion tube, a drive means for driving at least one of an advance/withdrawal means for advancing or withdrawing the insertion tube, a rotary means for rotating the insertion tube, and a bending means for bending the insertion tube, a drive control means for controlling the drive means, and an imaging means for produce images using a solid-state imaging device incorporated in the insertion tube, a conversion means for converting image signals originating from the imaging means into video signals, a video signal control means for controlling the conversion means, and a communication means for allowing the drive control means and video signal control means to communicate mutually.

Other features and advantages of the present invention will be apparent with the description below.

BRIEF DESCRIPTION OF THE DRAWINGS

FIG. 1 is an oblique view of the appearance of an endoscope system;

FIG. 2 is a block diagram for explaining the functional configuration of the endoscope system;

FIG. 3 is a flowchart showing control of the freeze and release functions;

FIG. 4 is a flowchart showing control of animated display on a subscreen in freeze or release mode;

FIG. 5 is an explanatory diagram for explaining how to produce panoramic images;

FIG. 6 is a flowchart showing control of panoramic display;

FIG. 7 is a configuration diagram outlining the configuration of the endoscope system;

FIG. 9 is a block diagram for explaining the functional configuration of the endoscope system;

FIG. 10 is an explanatory diagram for explaining the blur prevention function;

FIGS. 11 and 12 relate to the third embodiment;

FIG. 11 is a block diagram for explaining the functional configuration of the endoscope system;

FIG. 13 is a configuration diagram showing the configuration of the endoscope;

FIG. 14 is a block diagram for explaining control of the endoscope system; and

DETAILED DESCRIPTION OF THE PREFERRED EMBODIMENTS

Embodiments of the present invention will be described in conjunction with the drawings.

Figure 1:
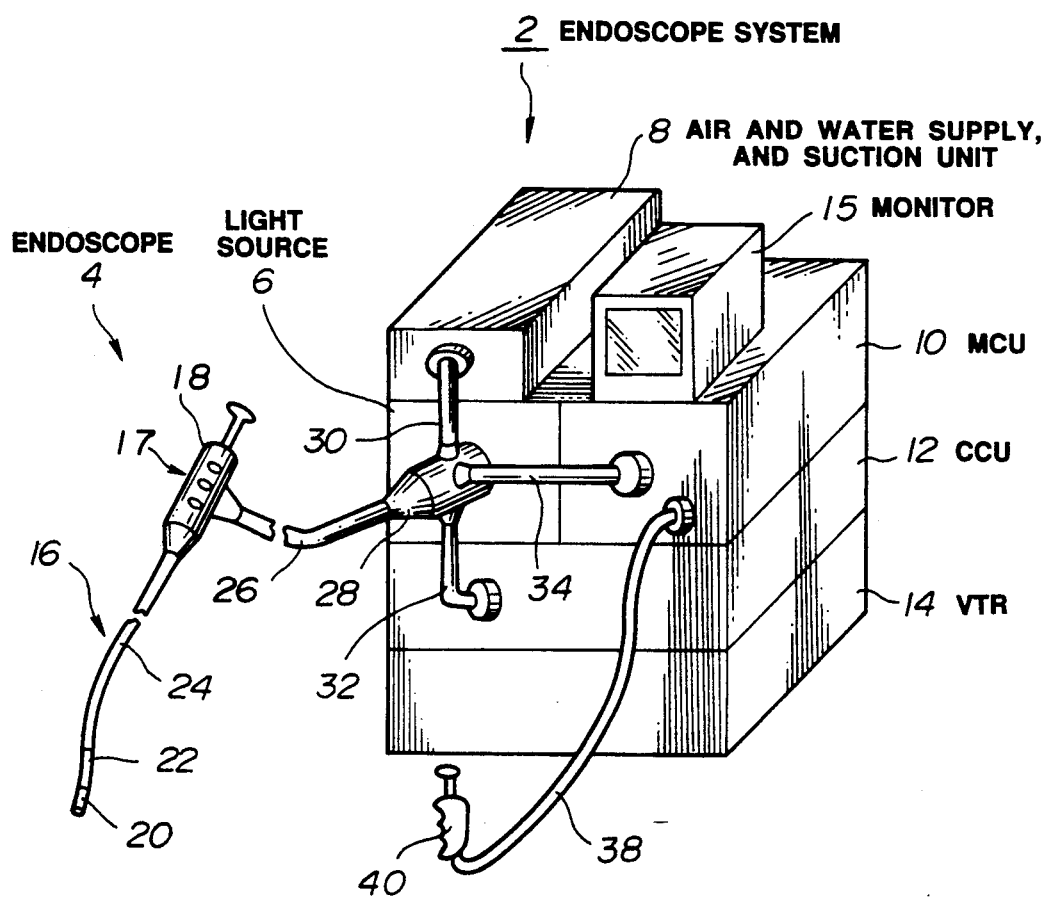
FIGS. 1 to 8 relate to the first embodiment.

As shown in FIG. 1, an endoscope system 2 of the first embodiment comprises, for example, an endoscope 4 to be inserted into body cavities, a light source 6 for supplying illumination light to the endoscope 4, an air and water supply, and suction unit 8 which supplies air and water to the endoscope 4, and sucks up, for example, contaminants from body cavities, a motor control unit (hereafter, MCU) 10 for driving and controlling a motor 57 to be described later for bending the endoscope, a camera control unit (hereafter, CCU) 12 for processing image signals originating from a solid-state imaging device installed at the distal end of the endoscope 4 and controlling the MCU 10, a monitor 15 for displaying video signals processed by the CCU 12, and a VTR 14 for recording the video signals. A remote control 40 for operating the MCU 10 remotely is connected to the MCU 10 via a remote control cable 38.

The endoscope 4 comprises an elongated insertion tube 16 having enough flexibility to run through body cavities, and an operator unit 18 which is formed at the proximal end of the insertion tube 16 and has a switch section 17 for controlling given operations. The insertion tube 16 includes a flexible section 24 whose proximal end is united with the operator unit 18, a bending section which is formed at the distal end of the flexible section 24 and driven to bend, and a distal end 20 formed at the tip of the bending section 22. The endoscope 4 is connected to the light source 6 via a universal cable 26 so that it can be disconnected freely by removing a connector 28.

Figure 2:
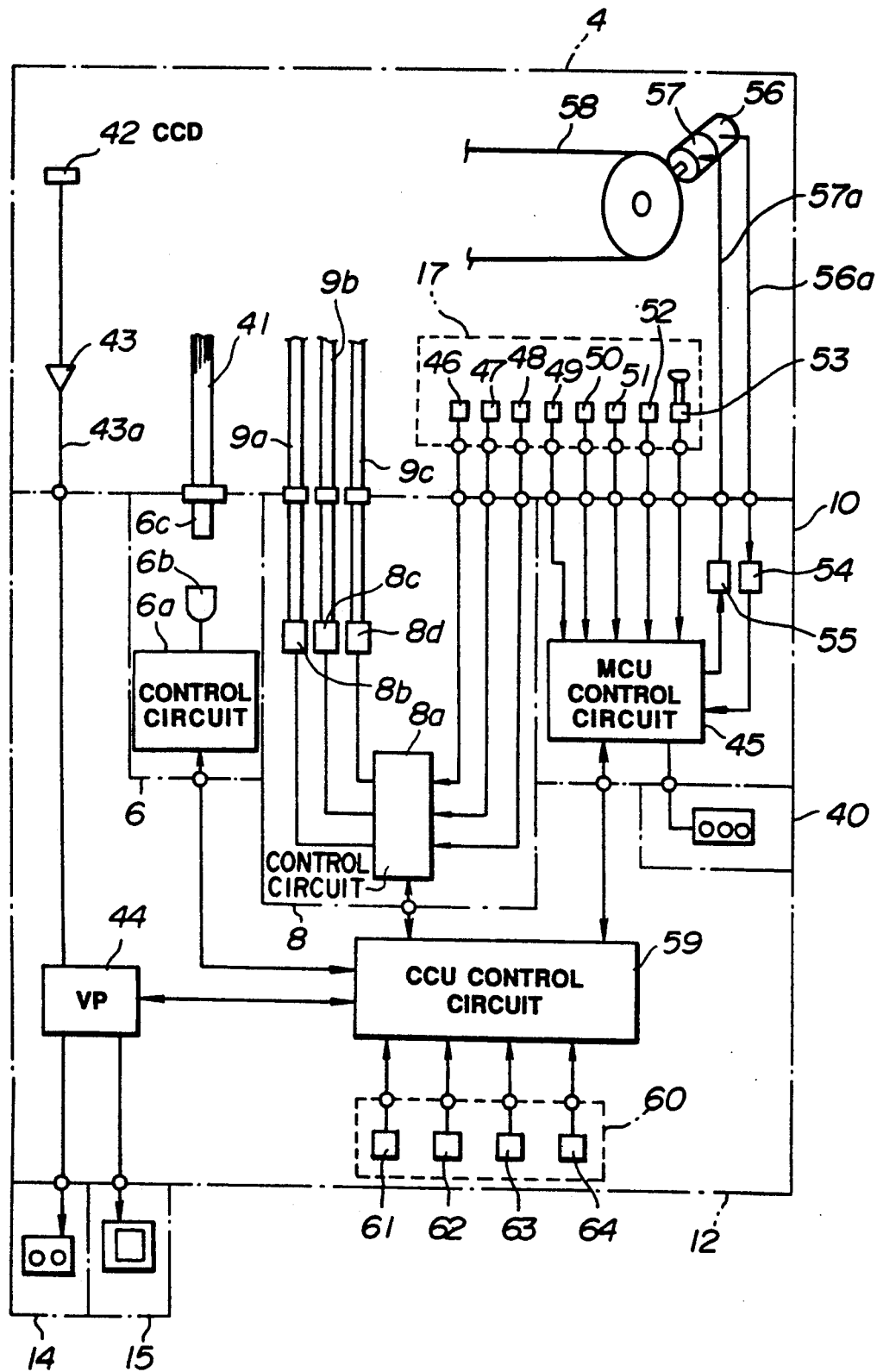

The universal cable 26 accommodates, as shown in FIG. 2, a light guide 41 for transmitting light emitted from the light source into the endoscope 4, an image cable 43a for transmitting image signals originating from a solid-state imaging device; such as, a simultaneous-type CCD 42 having a color filter array, incorporated in the distal end 20 of the endoscope 4 into the CCU 12, signal cables 56a and 57a for transmitting signals for driving and controlling the bending section 22 of the endoscope 4 from the MCU 10, and air and water supply, and suction pipes 9a, 9b, and 9c for supplying air and water from the air and water supply, and suction unit 8, and performing suction respectively. The universal cable 26 is coupled to the air and water supply, and suction unit 8, MCU 10, and CCU 12 via a connector 28 with cables 30, 32, and 34 respectively.

The light source 6 comprises a source lamp 6b, a control circuit 6a for controlling the source lamp 6b, and an emission light receptor 6c for receiving light from the source lamp 6b and transmitting it to the endoscope 4. The light source 6 emits emission light forward of the distal end 20 through the universal cable 26 and the insertion tube 16 of the endoscope 4. The distal end of the endoscope 4 incorporates the CCD 42 to produce images of subjects illuminated with emission light coming from the light source.

A produced image of a subject is converted into an image signal by a preamplifier 43 in the endoscope 4. Then, the image signal is provided to a video processor (hereafter, VP) 44 in the CCU 12 which decomposes the image signal and converts it to a video signal. The VP 44 outputs the video signal to the monitor 15 and VTR 14, as well as a camera recording unit which is not shown.

The air and water supply, and suction unit 8 controls air and water supply, and suction of the endoscope 4, comprising, for example, an air supply valve 8b formed with an electromagnetic valve, a water supply valve 8c, a suction valve 8d, and a control circuit 8a for controlling the air supply valve 8b, water supply valve 8c, and suction valve 8d. The control circuit 8a is connected to a Water switch 48 for indicating water supply, an Air switch 47 for indicating air supply, and a Suction switch 46 for indicating suction on the switch section 17.

The MCU 10 includes a driver 55 for driving via a drive cable 58 in the endoscope a motor 57 in the endoscope 4 to bend the bending section 22 vertically, and a bending angle detector circuit 54 for detecting a vertical bending angle of the bending section 22 by assessing a detection signal sent from an encoder 56 in the endoscope 4 which detects the rotating speed of the motor 57. For lateral bending, a driver for driving a bending motor to bend the bending section 22 laterally and a bending angle detector for detecting a lateral bending angle of the bending section 22 by assessing the rotating speed of the motor are provided.

Also provided is an MCU control circuit 45 which inputs detection signals from the bending angle detector circuit 54 and controls the driver 55. The MCU control circuit 45 is connected to a Bending switch 53, a Speed switch 52, a Free/Lock (hereafter, F/L) switch 51, an Angled Vibration (hereafter, AV) switch 50, and a Straight switch 49 on the switch section 17 formed in the operator unit of the endoscope 4.

The switches on the switch section 17 comprise the indication means and indicate given contents of control to the MCU 10. That is to say, the Bending switch 53, which is formed with, for example, a joystick, indicates to bend vertically or laterally the bending section 22 of the endoscope 4. The Speed switch 52 indicates a bending speed. The F/L switch 51 indicates whether curvature of the bending section 22 be released or retained. The AV switch 50 indicates fine angled vibration for the distal end of the endoscope 4. The Straight switch 49 indicates whether or not to straighten the bending section 22 to set the bending angle at zero. The Air switch 46, Water switch 47, or Suction switch 48 indicates given operations of air supply, water supply, or suction for the air and water supply, and suction unit 8.

The CCU 12 controls the VP 44, including a CCU control circuit 59 for communicating with the VP 44, a control 6a in the light source 6, a control 8a in the air and water supply, and suction unit 8, and the MCU control circuit 45. The CCU control circuit 59 is connected to a Freeze switch 61, a Release switch 62, a Panorama switch 63, and a Blur Prevention switch 64 on a switch section 60 formed in the CCU 12.

The switches on the switch section 60 comprise the indication means and indicate given contents of control to the CCU 12. That is to say, the Freeze switch 61 indicates, for example, whether or not to freeze fetching image data from frame memory (not shown) and actuate the freeze function to produce a still image. The Release switch 62 indicates whether or not the actuate the freeze function to produce a still image and record the still image using a camera recording unit which is not shown. The Panorama switch 63 indicates whether or not to actuate the panorama function for producing panoramic images which will be described later. The Blur Prevention switch 64 indicates whether or not to actuate the blur prevention function for preventing blur of images which will be described later.

Next, the functions of the endoscope system 2 having the foregoing configuration will be described.

First of all, control among the freeze or release function and other functions will be described.

Figure 3:
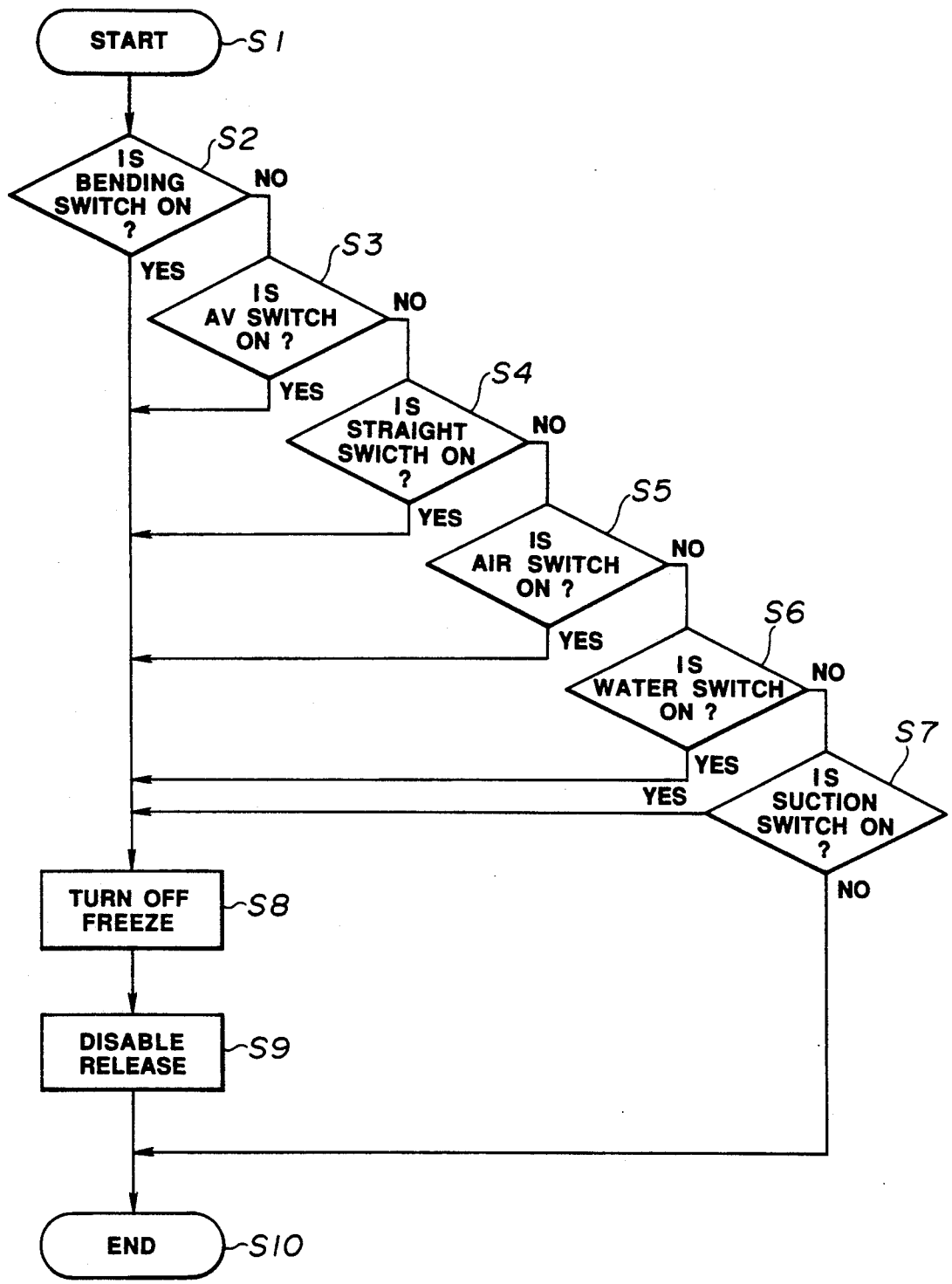

When switches on the switch section 60 are pressed to execute the freeze or release function, the process as shown in the flowchart of FIG. 3 is followed. After starting up at a step 1, the CCU control circuit 59 communicates with the MCU control circuit 45 at a step 2 and determines the state of the Bending switch 53. If the Bending switch 53 is on, the process is advanced to a step 8 to turn off the freeze function. At a step 9, the release state is disabled to display an animated image on the monitor 15. Then, the process is advanced to a step 10 and terminated.

At the step 2, if the Bending switch 53 is off, the CCU control circuit 59 communicates with the MCU control circuit 45 to determine the state of the AV switch 50 at a step 3 and the state of the Straight switch 49 at a step 4. Then, the CCU control circuit 59 communicates with the control 8a in the air and water supply, and suction unit 8 to determine the state of the Air switch 46 at a step 5, the state of the Water switch at a step 6, and the state of the Suction switch 48 at a step 7. When the switches are on, the CCU control circuit 59 advances to the step 8. When the switches are off, the CCU control circuit 59 advances to the step 10 and terminates.

Figure 4:
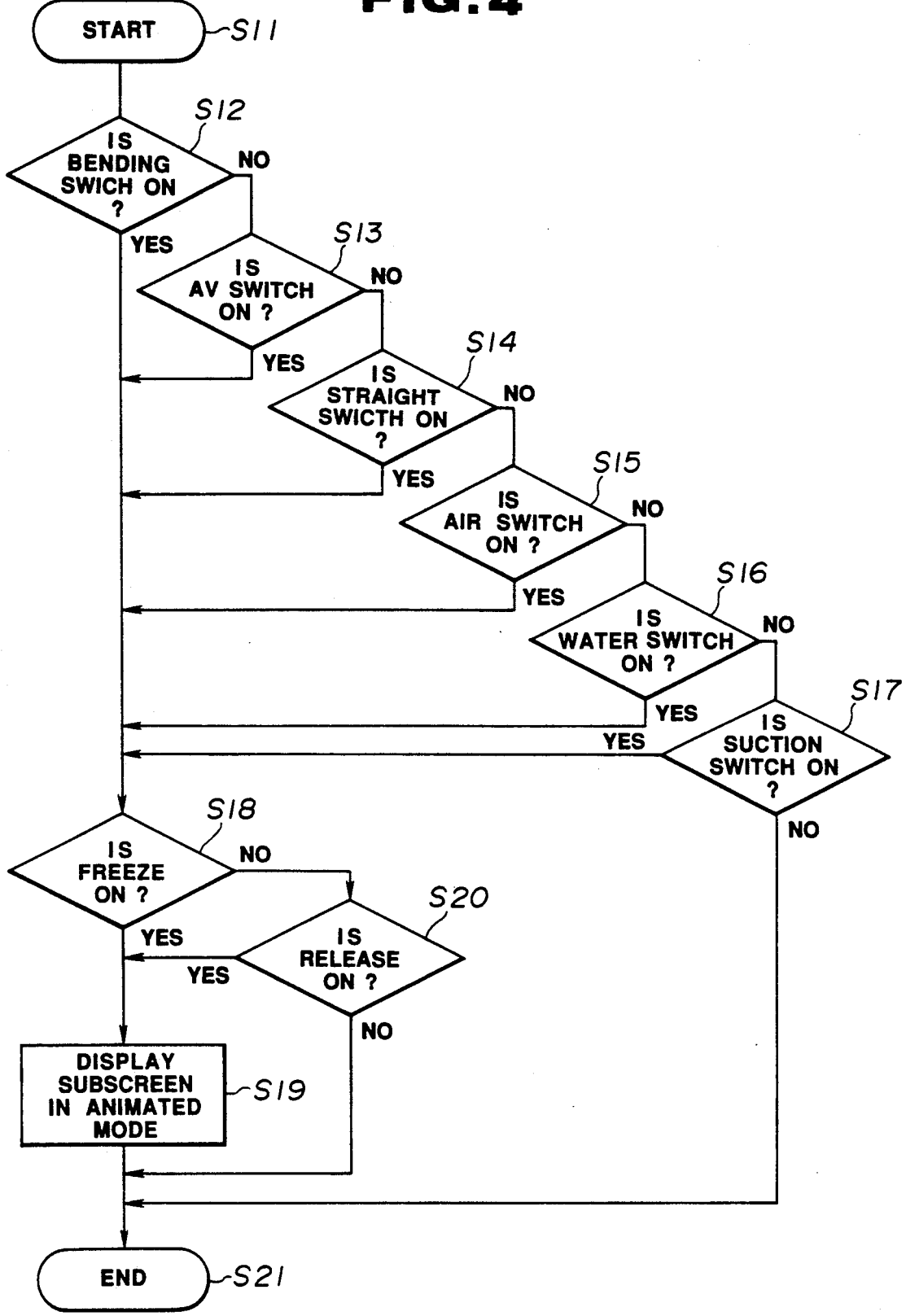

When a mode for displaying images on a subscreen of the monitor 15 has been selected using a mode select switch, which is not shown, if switches on the switch section 17 are pressed, the process shown in FIG. 4 is followed. After startup at a step 11, the state of the Bending switch is determined at a step 12. When the Bending switch 53 is on, it is determined at a step 18 whether the Freeze switch is on. If the Freeze switch is on, the process is advanced to a step 19. If the Freeze switch is off, the process is advanced to a step 20. At the step 19, a still image is displayed on the main screen of the monitor, and an animated image, on the subscreen of the monitor 15. Then, the process is terminated at a step 21. At the step 20, it is determined whether or not the release state is enabled. If the release state is enabled, the process is advanced to the step 19. If the release state is disabled, the process is advanced to the step 21.

When the Bending switch 53 is off at the step 12, the state of the AV switch is determined at the step 13, the state of the Straight switch 49, at the step 14, and the state of the Air switch, at the step 15. The state of the Water switch is determined at the step 16, and the state of the Suction switch 48, at the step 17. When the switches are on, the process is advanced to the step 18. When the switches are off, the process is advanced to the step 21 and terminated.

The MCU control circuit 45 communicates with the CCU control circuit 59 to determine the states of the Freeze switch 61 and Release switch 62. If the Freeze switch 61 or Release switch 62 is on, the MCU control circuit 45 stops the bending, AV, and straightening functions. The control 8a in the air and water supply, and suction unit 8 disables the operations of air and water supply, and suction.

Thus, the CCU control circuit 59, the MCU control circuit 45, and the control 8a in the air and water supply, and suction unit 8 communicate mutually. Then, when the endoscope 4 bends, a still image is switched to an animated image or an animated image is displayed on the subscreen. When the freeze function or release function is actuated, the endoscope is disabled to bend. This allows operators to carry out treatment or take action with ease and safety.

Figure 5:
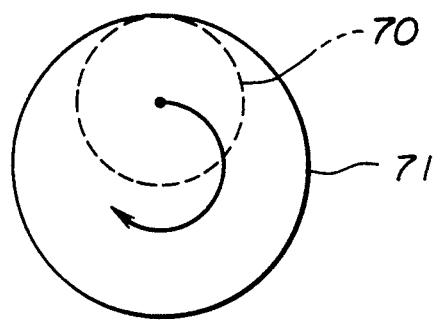

As shown in FIG. 5, a panoramic image is an image of an area 71 produced by executing an AV operation to rotate the distal end of the endoscope 4 in an arrow direction, then mixing the resultant images of an imaging area 70 of a CCD 42 indicated with a dotted line.

More specifically, assuming that the AV operation is executed at a speed of one rotation per ⅓ second and the acquisition time for a one-frame image is set to 1/30 second, images of ten frames can be acquired during a single rotation. The VP 44, for example, processes the images to retrieve consistent images from the images of ten frames and mix the retrieved images to produce a panoramic image.

Figure 6:
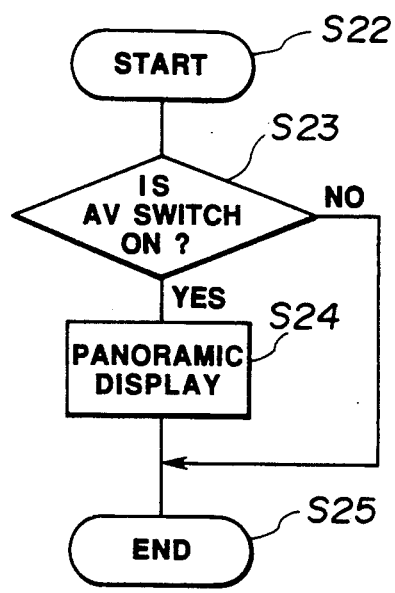

The display mode of a panoramic image is selected with a mode select switch which is not shown. As shown in FIG. 6, the CCU control circuit 59 communicates with the MCU control circuit 45, starts up at a step 22, then determines the state of the AV switch 50 at a step 23. If the AV switch 50 is on, the process is advanced to a step 24. At the step 24, the panoramic image is displayed on the monitor 15. Then, the CCU control circuit 59 terminates the process at a step 25. At the step 23, if the AV switch 50 is off, the CCU control circuit 59 advances the process and terminates it at the step 25.

Furthermore, the MCU control circuit 45 communicates with the CCU control circuit 59 to determine the state of the Panorama switch 63. If the Panorama switch 63 is on, the mode select switch, which is not shown, is used to select a mode for activating an AV operation.

The mode select switch, which is not shown, can be used to select various display modes in addition to the panoramic display mode. Other display mode that can be selected, for example, includes a mode for displaying only an image consistently formed in the imaging area 70 (See FIG. 5) of the CCD 42 when the tip of the endoscope 4 is finely rotated by an AV operation.

Even when a bending operation, for example, is under way instead of an AV operation, the CCU control circuit 59 communicates with the MCU control circuit 45. Then, using the mode select switch, which is not shown, a mode can be selected to display a panoramic image in the bending direction which has been produced by mixing images formed in the duration until the bending angle becomes equal to a given value. The MCU control circuit 45 communications with the CCU control circuit 59 to determine the state of the Panorama switch 63. Then, if the Panorama switch 63 is on, the mode select switch, which is not shown, is used to select a mode for achieving bending until a given angle is created.

Moreover, the select switch may be formed with a keyboard.

Thereby, operators can obtain various types of images; such as, panoramic images merely by selecting modes.

The CCU 12 displays a variety of information on the monitor 15 depending on with which the CCU control circuit 59 communicates; the MCU control circuit 45 or the control 8a in the air and water supply, and suction unit 8.

More specifically, assuming that the power supply of the MCU 10 is turned off, a signal originating from the MCU control circuit cannot be detected. Therefore, the CCU control circuit 59 determines that the power supply of the MCU 10 is off. Then, it outputs a given command to the VP 44 and displays such information as "MCU is off. Bending is disabled." or "Turn on the MCU power supply." on the monitor 15.

If the MCU 10 runs abnormally or other error occurs, it becomes impossible to communicate with the MCU control circuit 45. Therefore, the CCU control circuit 59 determines that the MCU 10 runs abnormally or other error occurs. Then, it issues a given command to the VP 44 and displays an error message indicating the contents of the error on the monitor 15 together with the information "MCU fails. Bending is disabled." According to the contents of an error, the error message varies; that is, "Overcurrent is flowing in the motor." or "An input signal from the encoder is abnormal."

Assuming that the power supply of the MCU 10 is turned on, communication with the MCU control circuit 45 is restarted. With an MCU 10 reset signal, the CCU control circuit 59 displays such information as "Execute UP bending." on the monitor 15.

The MCU control circuit 45 determines the state of the Bending switch 53. According to the state, it displays such information as drive control states on the monitor 15.

The MCU control circuit 45 determines the state of the F/L switch 51. According to the state, it displays information "Free" or "Lock" on the monitor 15.

In addition, the MCU control circuit 45 determines the state of the AV switch 50. If the AV switch 50 is on, information "AV is on" is displayed on the monitor 15. For an AV operation, a mode select means or a keyboard, which is not shown, for specifying the AV mode is used to set an AV-mode operation, an AV cycle, and an AV speed. According to the set values, appropriate information is displayed on the monitor 15. If clockwise rotation is specified as an AV-mode operation, information "CW" is displayed on the monitor 15. If the AV cycle is set to $\frac{1}{3}$ second, information "$\frac{1}{3}$-sec cycle" appears on the monitor 15. If the AV speed is 45 degree/sec, information "Speed 1" is displayed on the monitor 15.

The MCU control circuit 45 determines the state of the Speed switch 52. According to the speed, it displays such information as "Speed 1" on the monitor 15.

Based on an output of the bending angle detector circuit 54 for detecting a bending angle, such information as "UP 60°" is displayed on the monitor 15.

Bending resistance is identified, for example, when the MCU control circuit 45 detects power the driver 55 supplies to the monitor 57. Then, such information as "2, 4 W" is displayed on the monitor 15.

If the air and water supply, and suction unit 8 runs abnormally or other error occurs, it becomes impossible to communicate with the control 8a. Therefore, the CCU control circuit 59 determines that the air and water supply, and suction unit 8 runs abnormally or other error occurs. Then, the CCU control circuit 59 issues a given command to the VP 44 and displays an error message indicating the contents of the error on the monitor 15 together with information "The air and water supply, and suction unit malfunctions." The error message varies depending on the contents of an error. Such information as "The electromagnetic valve is defective," "Abnormal suction pressure," "Signal error," or "The suction container overflows with the content." is displayed on the monitor 15.

Furthermore, the states of the Air switch 46, Water switch 47, and Suction switch 48 are determined. According to the states, the control 8a in the air and water supply, and suction unit 8 controls the air supply valve 8b, water supply valve 8c, and suction valve 8d. Then, based on the result of communication with the CCU control circuit 59, the control 8a displays such information as "Air is being supplied," "Water is being supplied," or "Suction is under way" on the monitor 15.

Thus, since a variety of information appears on the monitor 15, operators can understand the state of the endoscope system 2 easily and take action properly.

Next, operations to be done when an image cannot be displayed on a monitor 15 will be described.

First, if the power supply of a CCU 12 is off, or if the CCU 12 runs abnormally or other error occurs, a MCU control circuit 45 cannot communicate with a CCU control circuit 59. Therefor, the MCU control circuit 45 determines that the power supply of the CCU 12 is turned off, or that the CCU 12 runs abnormally or other error occurs. As a result, the MCU control circuit 45 stops the bending, AV, and straightening functions.

When no image is displayed on the monitor 15 because of an illumination failure deriving from the fact that the power supply of the light source 6 has been turned off, the CCU control circuit 59 cannot communicate with a control circuit 6a in a light source 6. Therefore, the CCU control circuit 59 determines that the power supply of the light source 6 is turned off or other error occurs. Then, the CCU control circuit 59 issues a given command to a VP 44 and displays information "Illumination failure" on the monitor 15. At the same time, the CCU control circuit 59 communicates with the MCU control circuit 45, and stops the bending, AV, and straightening functions.

Thus, even when no image is displayed on the monitor 15, since all operations of an endoscope 4 are stopped, body cavities will never be injured.

An image signal of an image formed on a CCD 42 is input to the VP 44 via a preamplifier 43. The VP 44 determines if the brightness component of the input image signal is higher than a given threshold level. If it is higher, the VP 44 determines that the tip of the endoscope 4 is too close to a subject, and thereby the entire image is too bright to be visible. Then, the VP 44 transmits a given signal to the CCU control circuit 59. In response to the signal, the CCU control circuit 59 communicates with the MCU control circuit 45, then stops the bending, AV, and straightening functions.

Thus, even when an entire image is too bright to be visible, since all operations of the endoscope 4 are stopped, body cavities will never be injured.

The VP 44 detects the moistened state of a viewing window formed at the tip of the endoscope 4, then transmits a given signal to the CCU control circuit 59. In response to the signal, the CCU control circuit 59 communicates with the control circuit 8a in the air and water supply, and suction unit 8, then controls opening and closing of an air supply valve 8b, a water supply valve 8b, and a suction valve 8d to a given extent to remove moisture.

Therefore, operators can clearly view images formed on the CCD 42 without performing any special operation.

Moreover, when a Blur Prevention switch 64 is turned on, the CCU control circuit 59 communicates with the MCU control circuit 45 to be mentioned below and controls an MCU 10. That is to say, when the distal end 20 of the endoscope 4 comes close to a subject, or when a subject is viewed in enlarged scale, microscopic movement of the distal end 20 causes a displayed image to be blurred. To prevent this, the bending section 22 must be moved in a direction of counteracting blur of images. Specifically, based on an image signal of an image formed on the CCD 42, the VP 44 compares the image with an immediately preceding image to detect a deviating direction, then transmits the information to the CCU control circuit 59. Then, the CCU control circuit 59 communicates with the MCU control circuit 45, then controls the moving direction of the bending section so that a displayed image will not be blurred. This control is continued until deviation is dissolved.

Thus, images obtained are hardly deviated.

If a Priority switch, which is not shown, on a remote control 40 is under the control of the main unit of the endoscope 4, the CCU control circuit 59 communicates with the MCU control circuit 45 to determine the state of the Priority switch. Then, it displays on the monitor 15 such information as "The operator unit of the endoscope is given priority." In this case, the CCU control circuit 59 merely displays, for example, the operating state of the remote control 40 on the monitor 15. Actual bending control is subjected to operation of a switch section 17. According to the contents of control of the Bending switch on the remote control, for example, information such as drive control states is displayed on the monitor 15. Actual bending is controlled according to the state of operating switches on the switch section 17 in the operator unit 18 of the endoscope 4. Therefore, assuming that an expert operates the remote control 40 and a newcomer operates the switch section 17 of the endoscope 4, the newcomer can actually operate the endoscope 4 by himself/herself while referencing the expert's operation for each scene which is displayed on the monitor 15. This brings about numerous educational effects.

If the Priority switch, which is not shown, is under the control of the remote control 40, the MCU control circuit 45 determines the state of the Priority switch. Then, it displays on the monitor 15 such information as "The remote control is given priority.". In this case, the MCU control circuit 45, for example, not only displays "The remote control is given priority." but also controls various operations according to the operating information entered at the remote control 40. The operating information entered at the switch section 17 is ignored.

Thus, in the endoscope system 2 of the first embodiment, at least the CCU 12 and MCU 10 communicate mutually. This improves the system operability, allowing operators to operate the system easily. In addition, a variety of information displayed on the display monitor 15 not only helps upgrade operability and safety but also have great educational effects.

Figure 7:
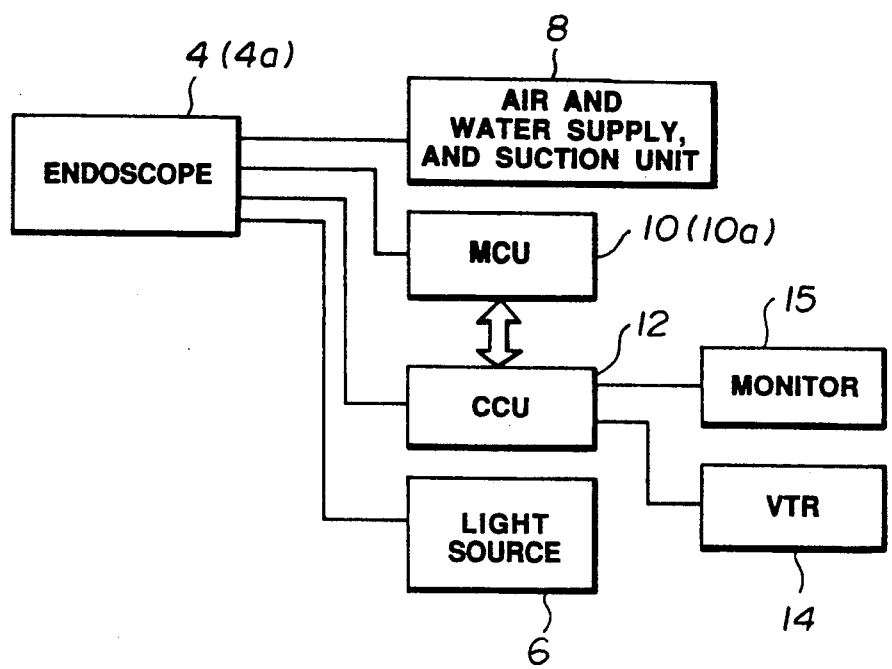
Figure 10:
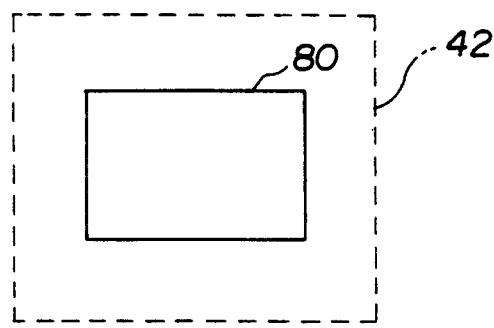
FIGS. 9 and 10 relate to the second embodiment.

The endoscope system comprises, as shown in FIG. 7, the endoscope 4 and a plurality of equipment having different functions which are connected to the endoscope 4; such as, the air and water supply, and suction unit 8, MCU 10, CCU 12, and light source 6. The CCU 12 includes, for example, the monitor 15, VTR 14, and camera recording unit which is not shown. However, the configuration of the endoscope system is not confined to this. On the contrary, as far as the MCU 10 and CCU 12 are designed to control each other, a plurality of sets of equipment having different functions may be connected to the endoscope 4 as a unit to constitute an endoscope system.

Figure 8A:
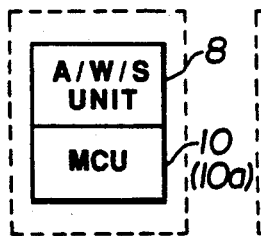
FIGS. 8A-N are block diagrams for explaining the functional configuration of the endoscope system.
Figure 8B:
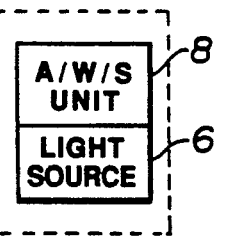
Figure 8C:
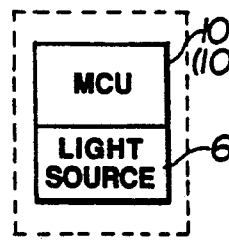
Figure 8D:
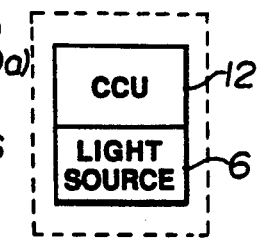
Figure 8E:
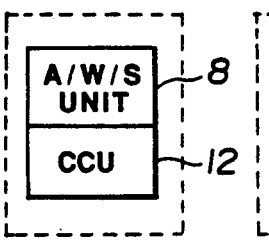
Figure 8F:
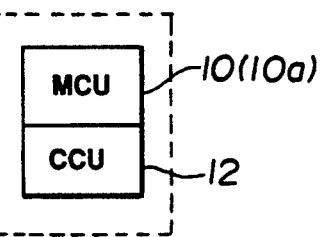
Figure 8G:
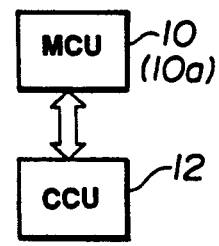
Figure 8H:
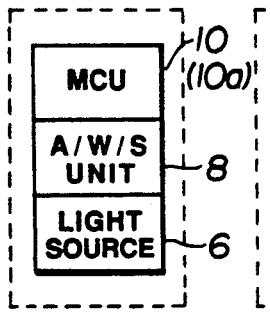
Figure 8I:
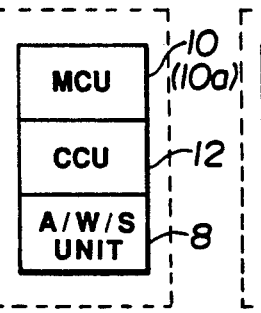
Figure 8J:
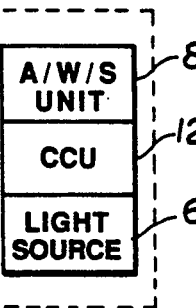
Figure 8K:
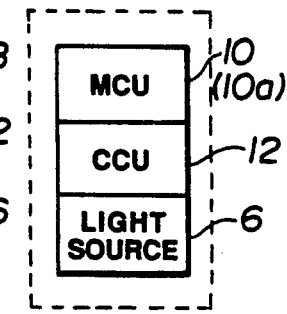
Figure 8L:
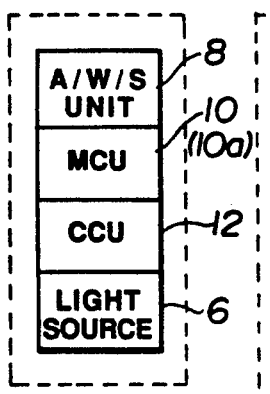
Figure 8M:
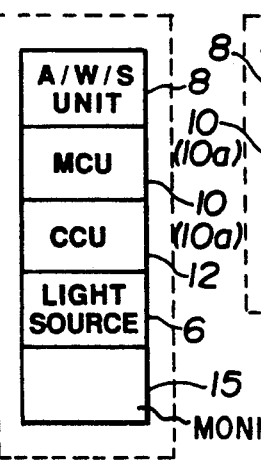
Figure 8N:
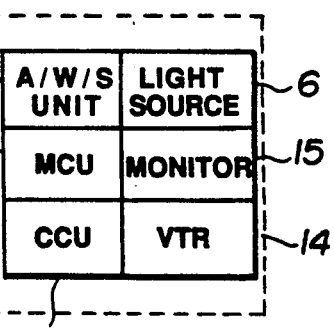

To be short, an endoscope system may be constructed by combining equipment to be connected to the endoscope 4 as a unit. The air and water supply, and suction unit 8 and MCU 10 may be combined as a unit as shown in FIG. 8A, the air and water supply, and suction unit 8 and light source 6, as shown in Figure B, the MCU 10 and light source 6, as shown in FIG. 8C, the CCU 12 and light source 6, as shown in FIG. 8D, the air and water supply, and suction unit 8 and CCU 12, as shown in FIG. 8E, the MCU 10 and CCU 12, as shown in FIG. 8F, or the MCU 10, air and water supply, and suction unit 8, and light source 6, as shown in FIG. 8I. Other conceivable combinations are the air and water supply, and suction unit 8, CCU 12, and light source 6 as shown in FIG. 8J, the MCU 10, CCU 12, and light source 6 as shown in FIG. 8, the air and water supply, and suction unit 8, MCU 10, CCU 12, and light source 6 as shown in FIG. L, the air and water supply, and suction unit 8, MCU 10, CCU 12, light source 7, and monitor 15 as shown in FIG. 8M, and the air and water supply, and suction unit 8, MCU 10, CCU 12, light source 6, monitor 15, and VTR 14 as shown in FIG. 8N. Furthermore, the camera recording unit may be added to the system shown in FIG. 8N.

The second embodiment of the present invention relates to an external motor-driven bending type endoscope system in which the bending motor for the first embodiment is installed outside an endoscope or, for example, in an MCU.

Components identical to those for the first embodiment will be assigned the same symbols. The description will be omitted.

Figure 9:
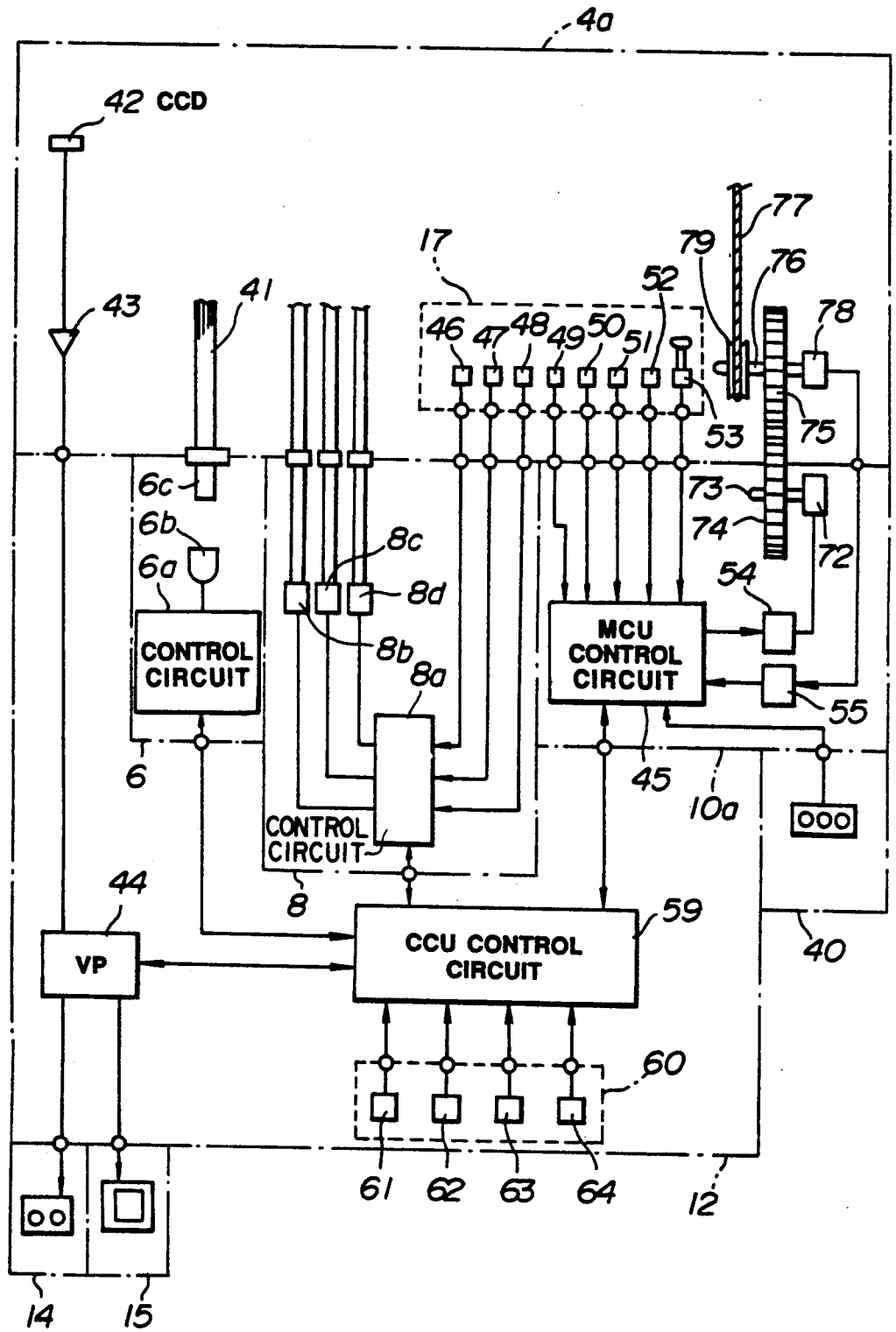
Figure 11:
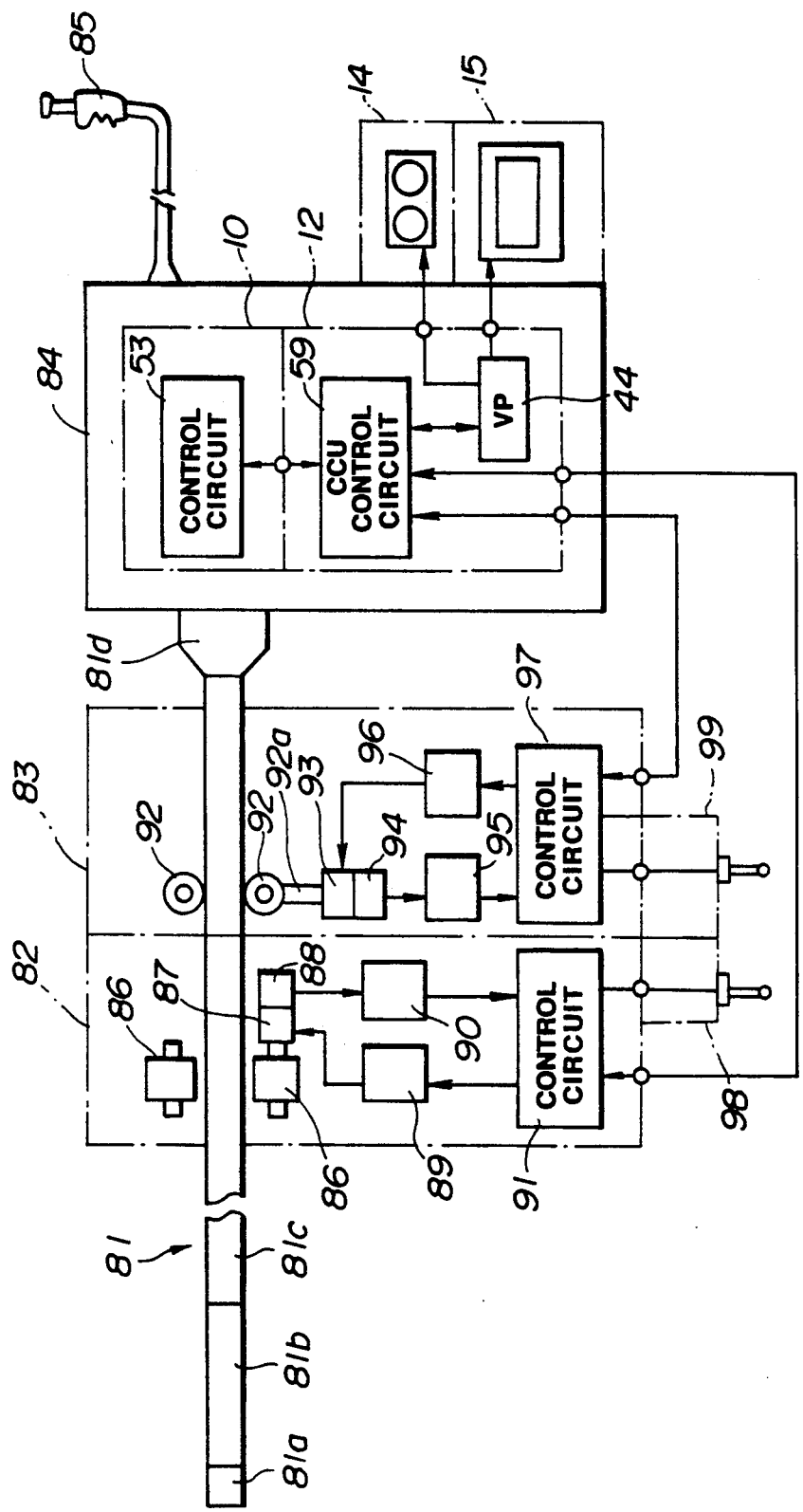

As shown in FIG. 9, a motor 72 for bending is arranged in an MCU 10a. A gear 74 is fixed to an axis 73 of the motor 72. A connector of an endoscope 4a, which is not shown, is connected to the MCU 10a firmly. The connector has a gear 75 to be engaged with the gear 74. A pulley 79 is fixed to an axis 76 of the gear 75, thus enabling to drive a bending cable 77. An encoder 78 is fixed to the axis 76 of the gear 75, so that a bending rate can be detected. Other components are identical to those for the first embodiment.

In the endoscope system of the second embodiment having the foregoing configuration, when a Blur Prevention switch 64 is turned on, a CCU control circuit 59 communicates with a MCU control circuit 45 as described below and controls an MCU 10. That is to say, a VP 44 cuts out part of all pixels generated by a CCD 42 or an area 80 alone, then displays it on a monitor 15. When a distal end 20 of an endoscope 4a deflects to cause an image to move within the CCD 42, the area 80 is moved within the pixels of the CCD 42 to follow the corresponding area of the image.

Thereby, even if the distal end 20 deflects, an image displayed on the monitor 15 will not be blurred.

Even when an AV switch, for example, is turned on instead of a Blur Prevention switch 64, the Blur Prevention process may be activated. As a result, even if the bending section 22 is angled and vibrated to cause the distal end 20 to deflect, an image displayed on the monitor 15 will not be blurred.

When a Panorama switch 63 is turned on, the CCU control circuit 59 communicates with the MCU control circuit as described below and controls the MCU 10. Specifically, when the CCU control circuit 59 determines that the Panorama switch 63 has been turned on, it asks the MCU control circuit 45 to control bending in the order that the bending section will be bent upward, straightened, bent downward, straightened, bent to the right, straightened, bent to the left, and straightened. The VP 44 fetches a plurality of images formed in these bending states, then mixes the images to produce a panoramic image.

The method of producing panoramic images is not limited to the aforesaid one. The method described in the first embodiment may be adopted (See FIG. 5).

The configuration of the endoscope system of the second embodiment (See FIG. 7), like that of the first embodiment, is not confined to the foregoing one. As far as the MCU 10a and CCU 12a are designed to control each other, units to be connected to the endoscope 4 may be a plurality of equipment having different functions which is combined as a unit (See FIG. 8).

Other functions and effects are identical to those for the first embodiment.

The third embodiment of the present invention has an insertion motor and a rotary motor as well as the bending motor for the first embodiment.

Components identical to those of the first embodiment will be assigned the same symbols. The description will be omitted.

To a control unit 84 formed by combining an MCU 10 and a CCU 12 as a unit, an endoscope 81 is connected via a connector 81d. The endoscope 8 comprises an insertion tube 81c whose proximal end is fixed to the connector 81d, a bending section 81b which is mounted at the tip of the insertion tube 81c to bend, and a distal end 81a formed at the tip of the bending section 81b.

At the proximal end of the insertion tube 81c, an advance/withdrawal MCUb 83 for advancing or withdrawing the endoscope 81 and a rotary MCUa 82 for rotating the endoscope 81 are connected and secured.

The advance/withdrawal MCUb 83 includes an advance/withdrawal drum 92 for advancing or withdrawing the endoscope 81. The advance/withdrawal drum 92 is connected to an advance/withdrawal motor 93 via a bevel gear and a shaft which are not shown. The advance/withdrawal motor 93 is driven by a driver 96. An encoder 94 for detecting an advancing/withdrawing speed is connected to the axis of the advance/withdrawal motor 93. The encoder 94 is connected to an inserting speed detector circuit 95. The driver 96 and inserting speed detector circuit 95 are connected to an advance/withdrawal control circuit 97.

The rotary MCUa 82 has a rotary drum 89 for rotating the endoscope 81. The rotary drum 86 is connected to a rotary motor 87 via a bevel gear and a shaft which are not shown. The rotary motor 87 is driven by a driver 89. An encoder 88 for detecting the rotating speed is connected to the axis of the rotary motor 87. The encoder 88 is connected to a rotating speed detector circuit 90. The driver 89 and rotating speed detector circuit are connected to a rotation control circuit 91.

Figure 12A:
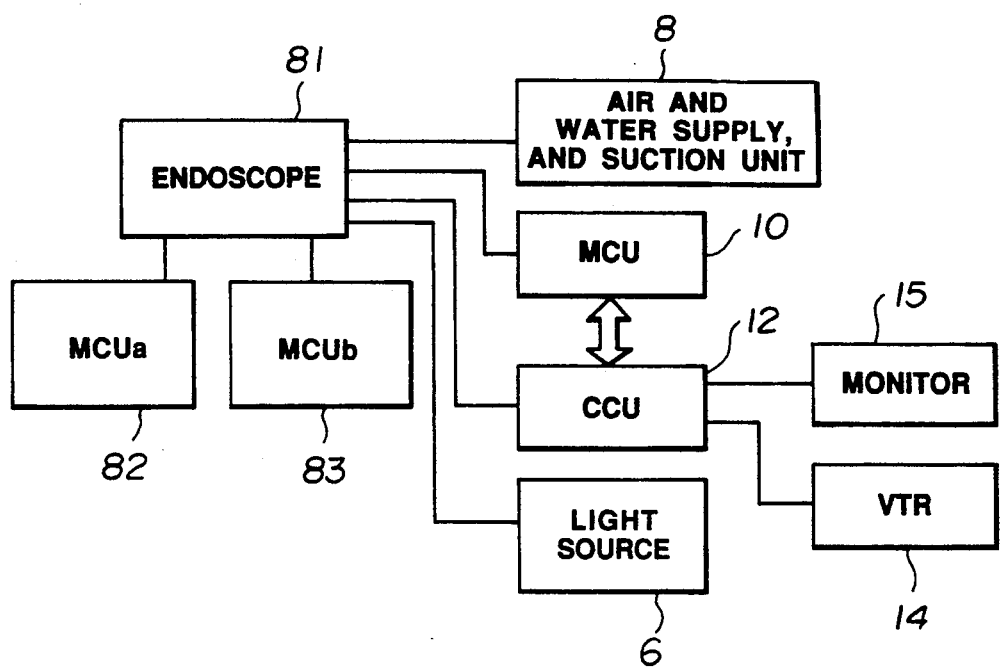
FIGS. 12A-B are configuration diagrams outlining the configuration of the endoscope system.
Figure 12B:
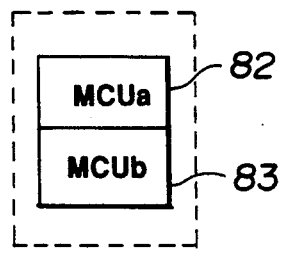

As shown in FIG. 12A, the endoscope system of the third embodiment has the same configuration as that of the first embodiment has but includes the advance/withdrawal MCUb 83 and rotary MCUa 82. The configuration of the endoscope is not limited to the foregoing one as described for the first embodiment. As far as the MCU 10 and CCU 12 are designed to control each other, a plurality of equipment having different functions can be connected as a unit to the endoscope 4a (See FIG. 8). As shown in FIG. 12B, the advance/withdrawal MCUb 83 and rotary MCUa 82 may be combined as a unit.

The advance/withdrawal control circuit 97 and rotation control circuit 91 can communicate with a CCU control circuit 59.

Other components are identical to those for the first embodiment.

The endoscope of the third embodiment having the foregoing configuration is almost the same as that of the first embodiment but includes the advance/withdrawal MCUb 83 for advancing or withdrawing an endoscope and the rotary MCUa 82 for rotating an endoscope. The advance/withdrawal MCUb 83 and rotary MCUa 82 are given almost the same functions as those of an MCU 10 by communicating with the CCU control circuit 59. The description of a bending function among the functions of the MCU 10 for the first embodiment is applicable to the advance/withdrawal function of the advance/withdrawal MCUb 83 as well as to the rotating function of the rotary MCUa 82. Therefore, the description of the advance/withdrawal and rotating functions will be omitted.

The advance/withdrawal MCUb 83 and rotary MCUa 82 may be combined as a unit and actuated simultaneously.

The CCU control circuit 59 may be provided with a lumen detecting function to control bending of the bending section 81b, so that the distal end 81a of the endoscope 81 will always face the center of a lumen. More specifically, the CCU control circuit 59 accesses an output of the VP 44 to detect the darkest area, communicates with the MCU control circuit 53 to determine in which direction the area is located with respect to the center of the CCD 42, then transmits the result to the MCU control circuit 53.

In response to the result transmitted, the MCU control circuit 53 bends the bending section 81b, for example, upward to the right. Then, when the darkest area coincides with the center of the CCD 42, the CCU control circuit 59 transmits a bending stop command to the MCU control circuit 53 in the MCU 10. Thereby, the bending section 81b stops and the distal end 81a faces the center of the lumen all the time.

The advance/withdrawal control circuit 97 in the advance/withdrawal MCUb 83 communicates with the CCU control circuit 59. When the output signal of the CCU control circuit 59 is a bending stop command, the endoscope 81 is inserted. When the output signal of the CCU control circuit 59 is a bending command, inserting the endoscope 81 is stopped to enable automatic insertion. The rotary MCUa 82 may be involved in automatic insertion.

Other functions and effects are identical to those for the first embodiment.

Figure 13:
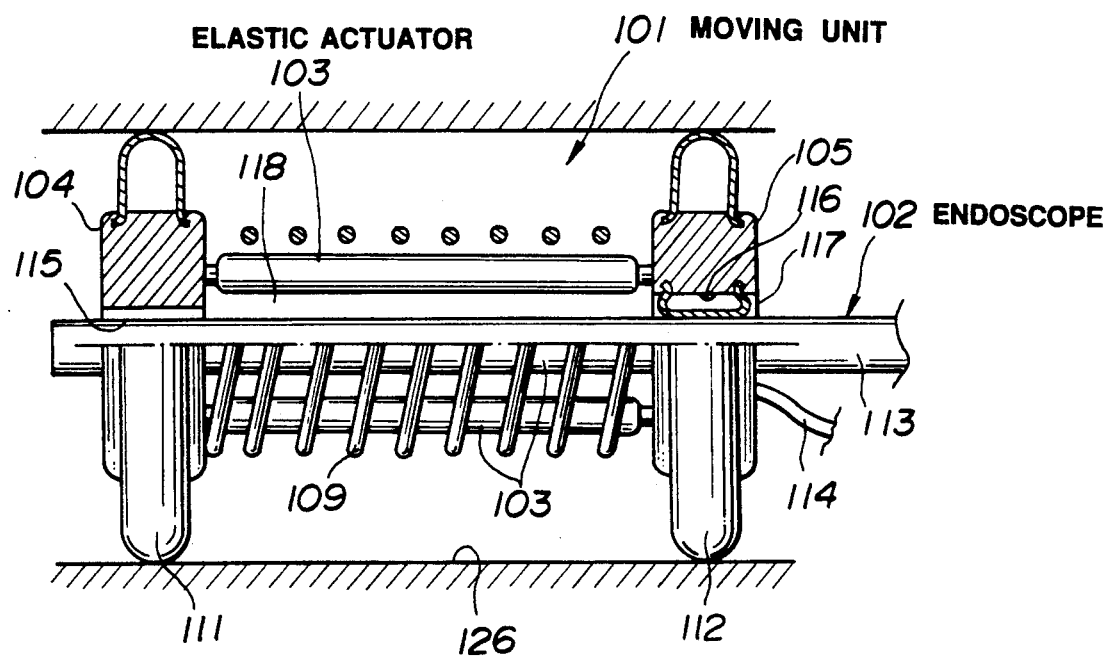
FIGS. 13 and 14 relate to the fourth embodiment.

The automatic intratubular running type endoscope system of the fourth embodiment includes, as shown in FIG. 13, a moving unit 101, and an endoscope 102 to be inserted under the guidance of the moving unit 101. The moving unit 101 includes a plurality of elastic actuators 103. When the elastic actuators 103 are provided with air or other pressure fluid by a pressure fluid supply means to be mentioned later, they elastically deform and dilate outward in the radial direction, and thus contract in the longitudinal direction.

The plurality of elastic actuators 103 is arranged vertically and laterally in parallel with the axial line of the moving unit 101 and in the surrounding area of the axial line. The tip of the elastic actuators 103 is locked in an anterior mounting member 104, and the back, in a posterior mounting member 105. These mounting members 104 and 105 are interposed by an elastic member 109 formed with a compression spring which generates force for pressing the elastic actuators 103 in the direction opposite to their contracting direction.

The elastic member 109 is located concentrically outside the elastic actuators 103. Moreover, balloons 111 and 112 or stoppage members are mounted in the circumferences of the mounting members 104 and 105. The balloons 111 and 112 dilate with pressure fluid supplied as mentioned later and become immobile on the internal surface of a duct 126 to be examined.

The elastic actuators 103, and balloons 111 and 112 in the moving unit 101 having the foregoing configuration receive or discharge pressure fluid through individual tubes 114.

The mounting members 104 and 105 in the moving unit 101 are provided with concentrically-penetrated through holes 115 and 116 to which the insertion tube 113 of an endoscope 102 or an inserted object can be inserted. The anterior and posterior through holes 115 and 116 serve as ends of an insertion passage 118 which penetrates through the moving unit 101 to route the insertion tube 113 of the endoscope 102 or an inserted object forward in the running direction.

The internal diameters of the through holes 115 and 116 are larger than those of the insertion tube 113 of the endoscope 102 or an inserted object. However, the posterior through hole 116 is formed larger than the anterior through hole 115.

A stoppage member 117 is mounted on the internal surface of the relatively larger posterior through hole 116 to immobilize the circumference of the insertion tube 113 of the endoscope 102. The stoppage member 117 is formed with a so-called balloon or film which is made from rubber or other elastic material and attached over the internal surface of the through hole 116 to create a sac. When the stoppage member 117 is filled with pressure fluid, it expands inward of the through hole 116 and presses the circumference of the insertion tube 113 of the endoscope 102 or an inserted object to immobilize the insertion tube 113.

Another tube 114 is connected to and routed inside of the stoppage member 117, thus supplying or discharging pressure fluid to or from the stoppage member 117. Thus, the stoppage member 117 formed in the posterior mounting member 105 serves as a holding means to immobilize or release an inserted object.

Figure 14:
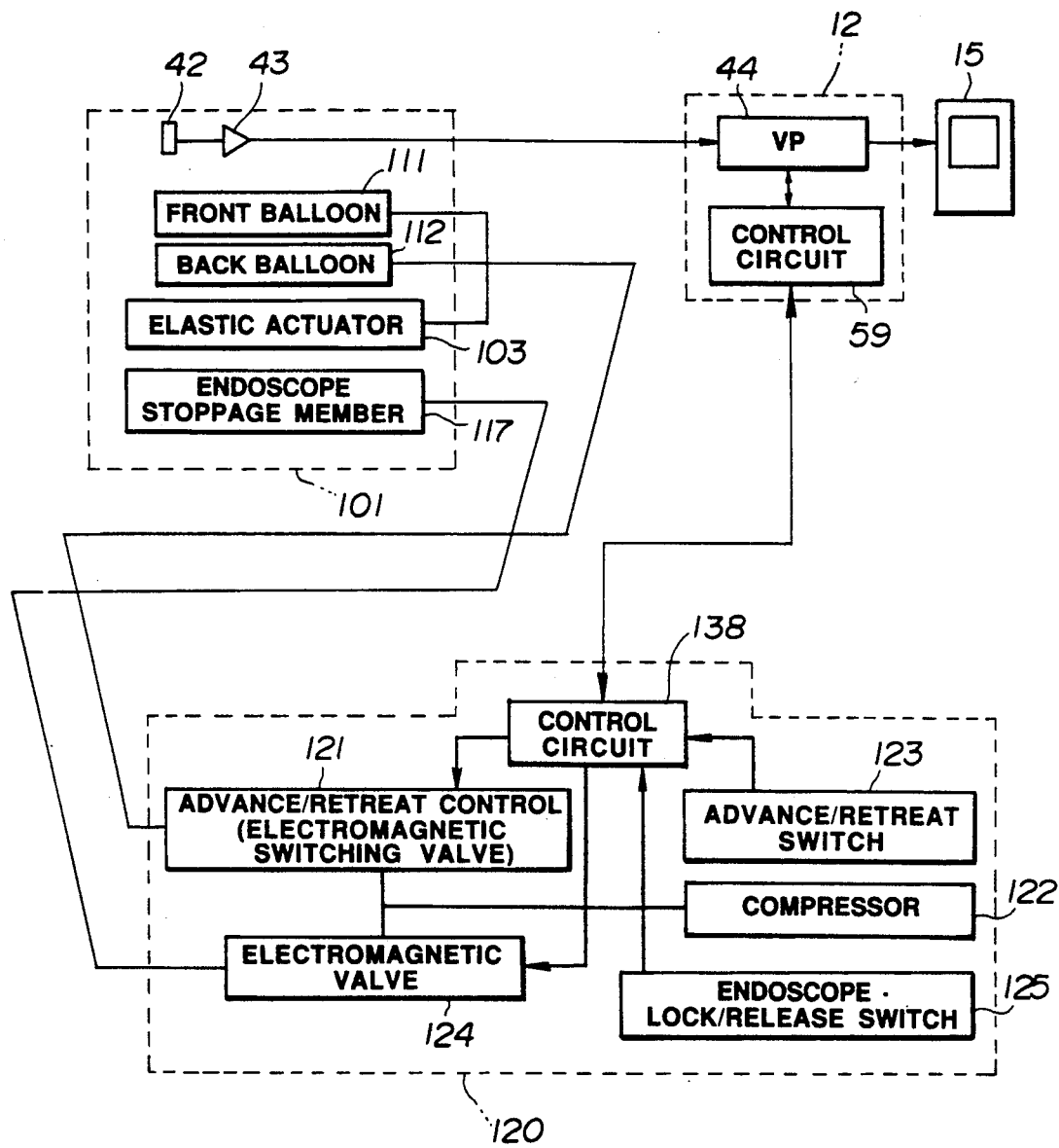

As shown in FIG. 14, the tubes 114 linking the elastic actuators 103 and balloons 111 and 112 in the moving unit 101 are connected to a compressor 122 via an electromagnetic switching valve of an advance/withdrawal control unit 121 incorporated in an extratubular operator unit 120. The operating mode for the electromagnetic switching valve of the advance/withdrawal control unit 121 is selected by a control circuit 138 having an advance/withdrawal control switch 123.

Another tube 114 entering the stoppage member 117 is connected to the compressor 122 via an electromagnetic valve 124. The electromagnetic valve 124 is operated by the control circuit 138 having an endoscope lock/release switch 125.

The control circuit 138 can communicate with the CCU control circuit in the CCU 12.

Next, an automatic running operation of the moving unit 101 will be described.

First of all, the moving unit 101 is placed in the entrance of a duct 126 to be examined with the balloons 111 and 112 contracted. Then, pressure fluid is supplied to the anterior balloon 111. Thus, the anterior balloon 111 is dilated and pressed to the internal circumferential surface of the duct 126, and thus immobilized. In this state, pressure fluid is supplied to the elastic actuators 103. Then, the elastic actuators 103 dilate in the radial direction but contract in the axial direction. This contracting force allows the posterior mounting member 105 to move forward. After the movement is complete, the posterior balloon 112 is dilated to stop on the internal circumferential surface of the duct 126. This immobilizes the posterior mounting member 105. After that, pressure fluid is discharged from the anterior balloon 11 and elastic actuators 103 in that order. Then, the anterior mounting member 104 is pressed forward by the elastic member 109. After the movement is complete, the anterior balloon 111 is dilated again. Then, pressure fluid is discharged from the posterior balloon 112. Then, the elastic actuators 103 are filled with pressure fluid, allowing the posterior mounting member 105 to move forward.

When the aforesaid operation is repeated, the moving unit 10 advances through the duct 126.

When the elastic actuators 103, and anterior and posterior balloons 111 and 112 are pressurized in the reverse order, the moving unit 101 withdraws.

Other components, functions, and effects are identical to those for the first embodiment.

In the fifth embodiment of the present invention, a shape memory alloy is made into a drive means to substitute for the motor in the first embodiment.

Components identical to those for the first embodiment will be assigned the same symbols. The description will be omitted.

Figure 15:
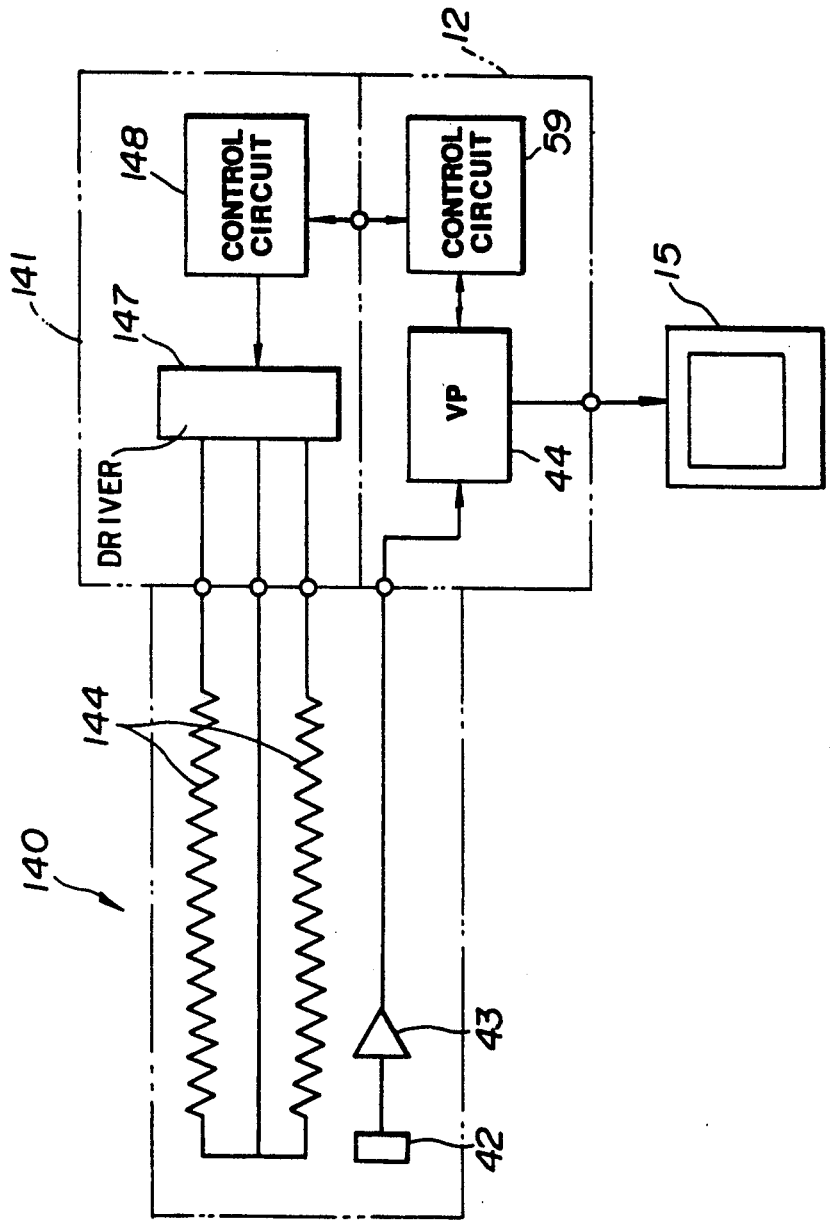
FIG. 15 is a block diagram for explaining the functional configuration of the endoscope system related to the fifth embodiment.

As shown in FIG. 15, a shape memory alloy (hereafter, SMA) 144 is incorporated as a bending drive means in an endoscope 140. When the SMA 144 is energized, it is connected to a driver 147 for bending in an SMA control unit 141. The driver 147 is connected to an SMA control circuit 148 for controlling bending. The SMA control circuit 148 communicates with a CCU control circuit 59. The driver 147 assesses electric energy supplied to the SMA 144 and thus detects a bending rate.

Other components, functions, and effects are identical to those for the first embodiment.

It will be apparent that different embodiments may be constituted based on the present invention without departing from the spirit and scope of the invention. The invention will be restricted by the appended claims but not by any specific embodiments.

What is claimed is:

1. An endoscope system, comprising:
    an endoscope having an insertion tube;
    a drive means for driving at least one of an advance and withdrawal means for advancing and withdrawing said insertion tube, a rotary means for rotating said insertion tube, and a bending means for bending said insertion tube;
    a drive control means for controlling said drive means;
    an imaging means for producing images using a solid-state imaging device incorporated in said insertion tube;
    a conversion means for converting image signals originating from said imaging means into video signals;
    a video signal control means for controlling said conversion means; and
    a communication means for allowing mutual operative communication between said drive control means and said video signal control means.

2. An endoscope system according to claim 1 wherein said drive control means uses said communication means to communicate with said video signal control means and thereby controls said video signal control means.

3. An endoscope system according to claim 2 wherein said video signal control means has an image freezing means for activating a freeze function, said drive control means disactivates said image freezing means upon actuation of said drive control means.

4. An endoscope system according to claim 1 wherein said video signal control means uses said communication means to communicate with said drive control means and thereby controls said drive control means.

5. An endoscope system according to claim 4 wherein said video signal control means has an image freezing means for activating a freeze function, said drive control means disactivates said driving means upon activation of said image freezing means.

6. An endoscope system according to claim 1 further comprising an indication means for indicating the contents of control to said drive control means or said video signal control means.

7. An endoscope system according to claim 6 wherein said drive control means or said video signal control means is actuated according to the contents of control indicated by said indication means, said communication means allows said video signal, control means and said drive control means to communicate with each other, and while one of the control means is in operation, the other control means is stopped.

8. An endoscope system according to claim 2, 4, or 7 further comprising a display means for displaying video signals originating from said conversion means.

9. An endoscope system according to claim 2, 4, or 7 further comprising a recording means for recording video signals originating from said conversion means.

10. An endoscope system according to claim 8 wherein said video signal control means displays drive control states on said display means.

11. An endoscope system according to claim 1 wherein said drive control means, said video signal control means, and said communication means are combined as a unit.

12. An endoscope system according to claim 1 further comprising a light source means for supplying illumination light to said endoscope and an air and water supply means for supplying air and water to said endoscope.

13. An endoscope system according to claim 12 wherein at least two of said drive control means, said video signal control means, said communication means, said air and water supply means, and said light source are combined as a unit.

14. An endoscope system according to claim 1 wherein said bending means has a shape memory member.

15. An endoscope system according to claim 1 further comprising a light source means for supplying illumination light to said endoscope and a fluid control means for controlling fluid in said endoscope.

16. An endoscope system according to claim 15 further comprising an indication means for indicating the contents of control of at least one of said drive control means, said video signal control means, and said fluid control means.

17. An endoscope system according to claim 16 wherein said communication means permits communication with each of said control means according to the contents of control indicated by said indication means, wherein if a control means other than that indicated by said indication means is in operation, an operation indicated by said indication means is disabled, and if any other control means is not operating, an operation indicated by said indication means is executed.

18. An endoscope system according to claim 16 wherein said communication means permits communication with each of said control means according to the contents of control indicated by said indication means, wherein if a control means other than the one indicated by said indication means is in operation, an operation indicated by said indication means is executed, and if any other control means is not operating, an operation indicated by said indication means is disabled.

19. An endoscope system according to claim 15 further comprising a display means for displaying video signals originating from said conversion means, wherein said video signal control means uses said communication control means to communicate with said drive control means, said fluid control means, and said light source means, and wherein if communication with at least one of drive control means, said fluid control means, and said light source means is suspended, said video signal control means controls said display means so that the communication state will be displayed.

20. An endoscope system according to claim 15 wherein said video signal control means uses said communication means to communicate with said drive control means, said fluid control means, and said light source means, and wherein if communication with at least one of said drive control means, said fluid control means, and said light source means is suspended, said video signal control means disables control by said drive control means.

21. An endoscope system according to claim 15 wherein said video signal control means uses said communication means to communicate with said drive control means, said fluid control means, and said light source, and wherein if said communication means detects error information in communications among said video signal control means, said drive control means, said fluid control means, and said light source means, said communication means uses at least said drive control means to disable control.

22. An endoscope system according to claim 15 wherein said video signal control means uses said communication means to communicate with said drive control means, said fluid control means, and said light source, and wherein if said communication means detects error information in communications among said video signal control means, said drive control means, said fluid control means, and said light source means, said communication means communicates with each control means and asks the control means to resolve the error.

23. An endoscope system according to claim 16 wherein said communication means is used to communicate with each of said control means according to the contents of control indicated by said indication means, and when control of said indication means is complete, said communication means communicates with each control means to stop their control operations.

24. An endoscope system control method, comprising:
 a driving procedure for executing at least one of an advance and withdrawal procedure for advancing and withdrawing an insertion tube of an endoscope, a rotating procedure for rotating a rotary means for rotating said insertion tube, and a bending procedure for bending said insertion tube;
 a drive control procedure for controlling said driving procedure;
 an imaging procedure for forming images using a solid-state imaging device incorporated in said insertion tube;
 a conversion procedure for converting image signals originating from said imaging procedure into video signals;
 a video signal control procedure for controlling said conversion procedure; and
 a communication procedure for allowing a mutual operative communication procedure between said drive control procedure and said video signal control procedure.

25. An endoscope system control method according to claim 24 wherein said drive control procedure uses said communication procedure to communicate with said video signal control procedure and thereby controls said video signal control procedure.

26. An endoscope system control method according to claim 25 wherein said video signal control procedure includes an image freezing procedure, said drive control procedure stops said image freezing procedure upon activation of said drive control procedure.

27. An endoscope system control method according to claim 24 wherein said video signal control procedure uses said communication procedure to communicate with said drive control procedure and thereby controls said drive control procedure.

28. An endoscope system control method according to claim 27 wherein said video signal control procedure includes an image freezing procedure, said drive control procedure stops said driving procedure when said image freezing procedure is activated.

29. An endoscope system control method according to claim 24 further comprising an indication procedure for indicating the contents of control to said drive control procedure or said video signal control procedure.

30. An endoscope system control method according to claim 29 wherein said drive control procedure or said video signal control procedure is activated according to the contents of control indicated by said indication procedure, said communication procedure allows said video signal control procedure and said drive control procedure to communicate with each other, and when one of the control procedures is in operation, the other control procedure is stopped.

31. An endoscope system control method according to claim 25, 27, or 30 further comprising a display procedure for displaying video signals originating from said conversion procedure.

32. An endoscope system control method according to claim 25, 27, or 30 further comprising a recording procedure for recording video signals originating from said conversion procedure.

33. An endoscope system control method according to claim 31 wherein said video signal control procedure displays drive control states in said display procedure.

34. An endoscope system control method according to claim 24 further comprising a light source procedure for supplying illumination light to said endoscope and an air and water supply procedure for supplying air and water to said endoscope.

* * * * *